United States Patent [19]

Girolami

[11] Patent Number: 4,612,801
[45] Date of Patent: Sep. 23, 1986

[54] COAGULOMETER AND METHOD OF MEASURING OF THE TIME OF COAGULATION OF SAMPLES OF FLUID PRODUCTS

[76] Inventor: Antoine Girolami, La Plaine, Route de Lascours, 13400 Aubagne, France

[21] Appl. No.: 747,524

[22] Filed: Jun. 21, 1985

[30] Foreign Application Priority Data

Jun. 27, 1984 [FR] France .................. 84 10427

[51] Int. Cl.$^4$ ................ G01N 33/48; G01N 11/10
[52] U.S. Cl. .................................. 73/64.1
[58] Field of Search .................. 73/64.1; 356/39

[56] References Cited

U.S. PATENT DOCUMENTS

| | | | |
|---|---|---|---|
| 3,714,815 | 2/1973 | Hartert | 73/64.1 |
| 3,967,934 | 7/1976 | Seitz et al. | 73/64.1 X |
| 4,081,242 | 3/1978 | Girolami | 73/64.1 X |

FOREIGN PATENT DOCUMENTS 2516658  5/1983  France .................. 73/64.1

Primary Examiner—Stewart J. Levy
Assistant Examiner—Joseph W. Roskos
Attorney, Agent, or Firm—William A. Drucker

[57] ABSTRACT

Method of measuring the time of coagulation of samples of fluid products such as, for example, samples of blood plasma, wherein the dose of liquid substance to be analyzed is introduced into a small cup (1) the base (1a) of which is shaped to serve as a circular rolling path (1b) for a ball (2) disposed in the lower part of the cup which is actuated with a non-rotary circular movement be means of an eccentric (3-3a) causing a rotation of the ball in a circular path in the base of the cup. The gradual slowing and/or halting of the rotary movement of the ball caused by the thickening or coagulation of the sample of the medium or liquid substance contained in the cup, for example following the introduction of a reactant, is ascertainable visually or, preferably, by any suitable automatic detection system.

12 Claims, 7 Drawing Figures

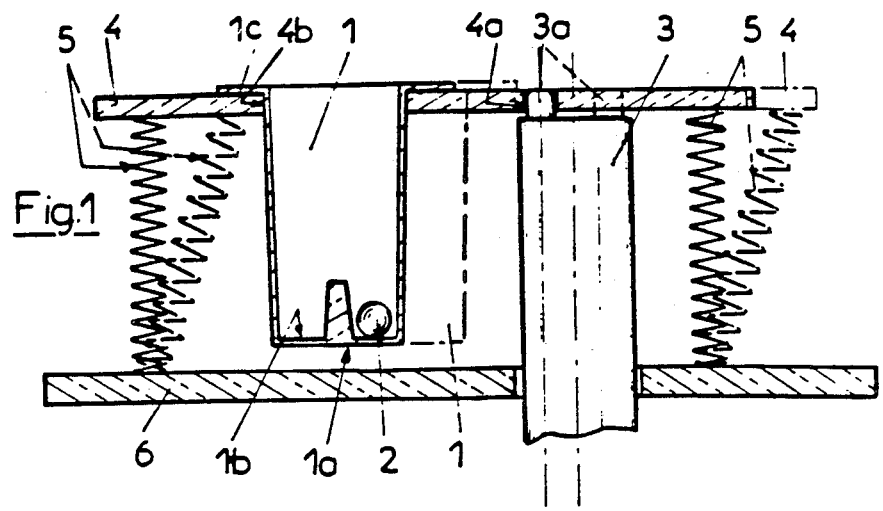
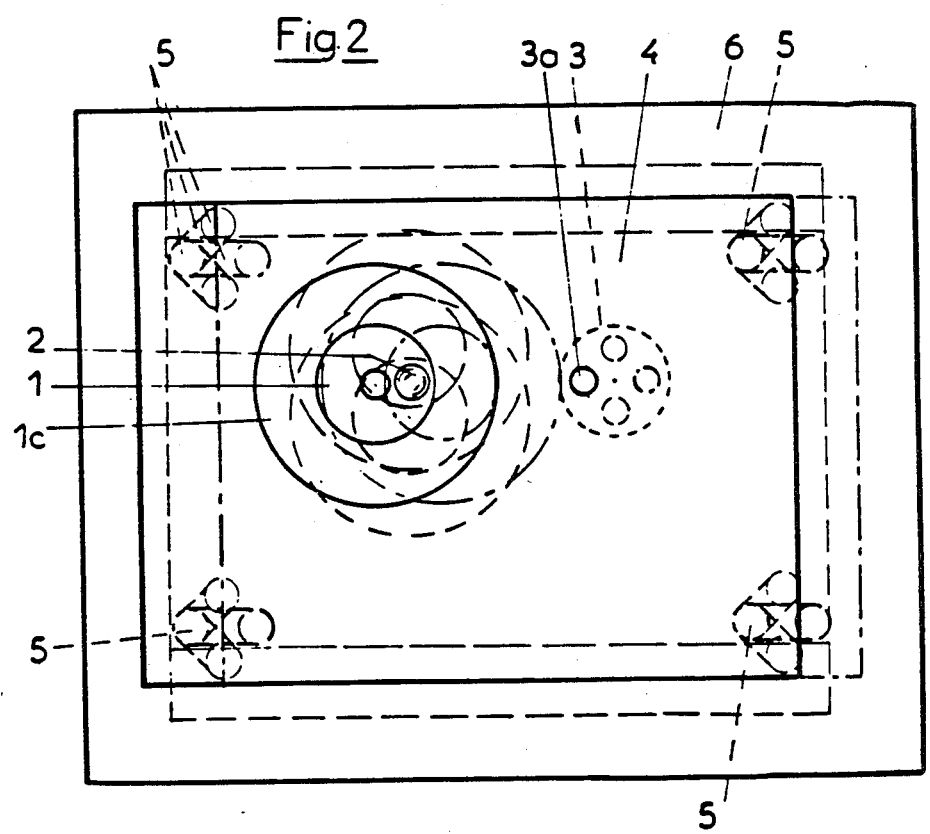

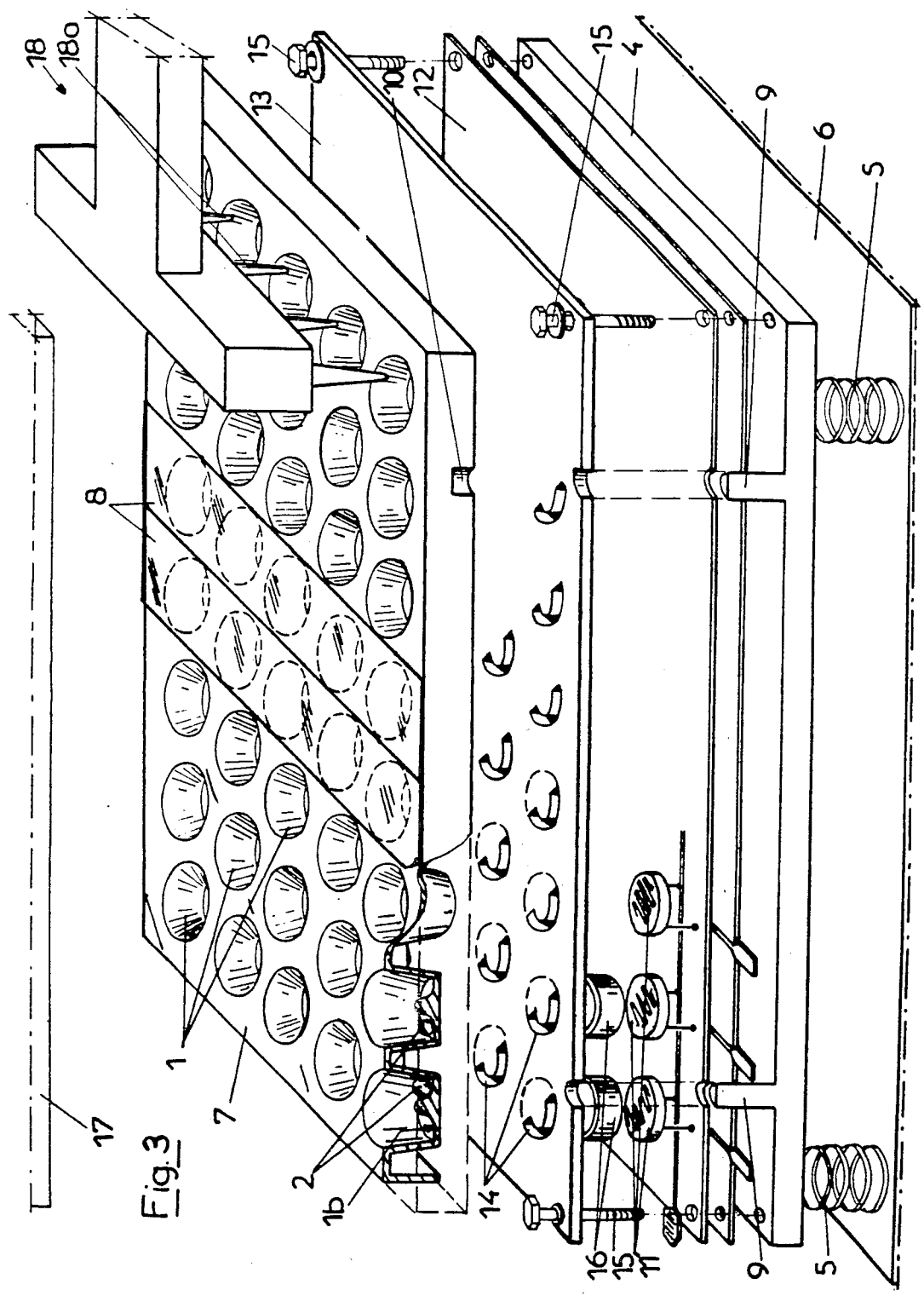

COAGULOMETER AND METHOD OF MEASURING OF THE TIME OF COAGULATION OF SAMPLES OF FLUID PRODUCTS

BACKGROUND OF THE INVENTION

The present invention relates to an apparatus for measurement of the time of coagulation of samples of fluid products and more particularly a coagulometer for the determination of the time of coagulation of samples of blood plasmas or other coagulation tests.

It likewise relates to the method put into operation to carry out this measurement of the coagulation time.

More precisely, the invention relates to a coagulometer of the kind comprising at least one cup or, more often, a plurality of cups in the base of which is positioned a ball activated with a movement of rotation in a circular rolling path formed in the base of the said cups.

PRIOR ART

In the known apparatuses of this kind (FR-A-No. 2318421), each cylindrical cup is placed in an inclined position and can be driven in rotation about its inclined axis, such that after introduction of a sample of blood plasma into the said cup, the ball rotates on the spot and remains, by gravity, in a sloping position so long as the same remains in the liquid state, whilst it is driven in a circular movement about the axis of the cup at the time of formation of the coagulum, this change of position of the ball in space being ascertained visually or by any appropriate automatic detection system.

The known apparatus of this kind permit the carrying out of precise, reproducible and simultaneous measurements. Nevertheless, after several years of use, it has been found that they were affected by a certain number of deficiencies which it was desirable to remedy.

One of these deficiencies arises from the fact that it is difficult to manufacture apparatuses permitting the carrying out of numerous simultaneous determinations, because of the necessity to drive each cup individually in rotation, and because of the inclined positioning of the assembly of cups.

Another deficiency of the apparatus of this type results from the fact that by reason of the inclination of each cup, it is difficult to determine the ideal weight of the ball to be retained, as a function of the physicochemical characteristics of the sample of medium analysed.

Another deficiency of the apparatus of this kind resides in the fact that it is almost impossible to interrupt the rotation of the cup, and to start it up again in the course of the same determination (for example for the determination of the Howell period).

Another important failing of these apparatus arises from the fact that they do not give any intermediate information on the formation of the coagulum, between start and finish of the measurement, which results in effect from the simple detection of the abrupt change of position of the ball in space when the coagulum is formed.

Furthermore, it is difficult to equip this kind of apparatus with systems for the automatic introduction of analysed media and reactants, particularly when it is a case of apparatus intended to carry out a plurality of tests simultaneously.

OBJECT OF THE INVENTION

The present invention has for its object a method and an apparatus remedying the above-mentioned deficiencies of materials operating by detection of the position of a ball positioned in the base of a cup, and permitting release from a certain number of constraints imposed by this kind of materials.

SUMMARY OF THE INVENTION

According to the invention, this object is achieved by means of a method in accordance with which the sample of liquid medium or product to be analysed is introduced into a small cylindrical or frusto-conical cup the base of which is shaped to serve as a circular rolling path for a ball disposed in the lower part of the said cup, which is actuated with a non-rotary circular movement, by means of an eccentric, causing a rotation of the ball along a circular trajectory, in the base of the cup, the gradual slowing and/or halting of the rotary movement of the said ball, caused by the thickening or coagulation of the said medium, for example following the introduction of a reagent or other chemical substance, being ascertainable visually or, preferably, by any other suitable system of automatic detection.

The coagulometer in accordance with the invention is mainly notable for the fact that it comprises: at least one cup or, preferably, an assembly constituted of several cups the base of which is shaped to serve as a circular rolling path for a ball disposed in the said cup or in the said cups;

an eccentric device permitting to communicate a non-rotary circular movement to the cup or to the said assembly of cups;

and means ensuring guiding of the said cup or the same assembly of cups during its non-rotary circular movement.

The method and apparatus in accordance with the invention provide a number of important advantages.

This method offers the possibility of placing simultaneously in movement, by means of a single eccentric device, a large number of cups installed on a single support. These cups can be positioned vertically, such that the circular path of rolling of the ball is placed in a horizontal plane. The systems for detection of movement of the ball disposed in each cup can thus be placed above the cups. It is thereby possible to construct apparatus permitting the carrying out, simultaneously, of a large number of tests or analyses. On the other hand, the method and the apparatus according to the invention permit the establishment of diagrams of the deceleration of the circular movement of the ball as a function of the progressive thickening of the medium analysed, this pemitting the carrying out of analyses of very great precision on the process of formation of the coagulum for the whole of the duration of the tests. The intermediate results which it is thus possible to obtain can be very interesting and numerous, especially in the application of the method and apparatus to the analysis of the time of coagulation or prothrombin or other coagulation tests with blood, when it is known that these results will serve as a basis for the prescription of medical treatments.

Another advantage of the method and coagulometer according to the invention resides in the fact that the weight of the ball has hardly any importance and does not constitute a factor disturbing the precision of the measurements. The cups can be positioned in advance on a support plate produced with openings serving to receive them, or moulded at the same time as the said support plate, in such a manner as to constitute standardised assemblies composed of a predetermined number of cups. The balls can be placed in advance in the cups which, after sterilisation, can be sealed off by means of a detachable tape. It is thus possible to use only a part of the cups constituting a plate of cups. On the other hand, the presentation of the cups in the form of plates or tablets faciitates thermostatting them at the desired temperature before and/or during their use.

BRIEF DESCRIPTION OF THE DRAWINGS

The above-mentioned objects, features and advantages, and others as well, will be better appreciated from the following description and the accompanying drawings, in which:

FIG. 1 is a view in elevation and in section of a very simplified form of construction of the coagulometer in accordance with the invention, the chain-dotted line indicating the position of the movement members of the apparatus after a non-rotary circular movement of 180°;

FIG. 2 is a plan view of FIG. 1, the broken lines indicating the successive positions of the movable members of the apparatus after non-rotary circular movements respectively of 90°, 180° and 270°;

FIG. 3 is a view in perspective, with the parts shown separated, of a coagulometer intended to carry out a plurality of simultaneous analyses and equipped with an optical detection system;

DESCRIPTION OF THE PREFERRED EMBODIMENTS

Figure 4:
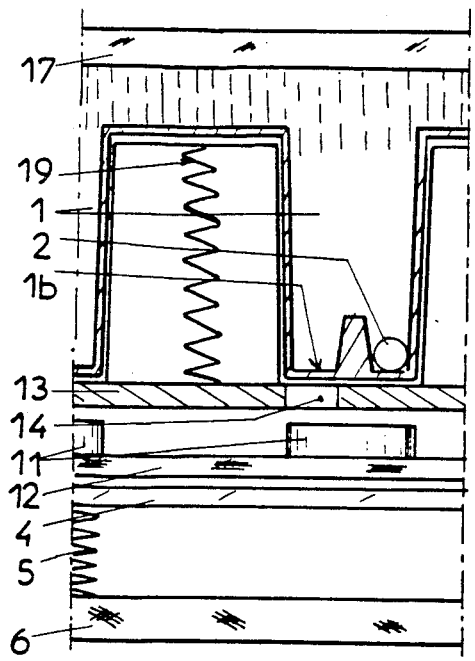
FIG. 4 is a partial view, in elevation and in section, of a modification of construction of this apparatus.

Reference is made to the said drawings to describe advantageous, although in no way limiting, examples of carrying out the method and constructions of the apparatus of the invention.

Reference is firstly made to FIGS. 1 and 2 which illustrate an extremely simplified manner of construction of this apparatus, comprising in this case only a single cup, and which has principally for its object to facilitate the understanding of the carrying out of the method and of the operation of the coagulometer of the invention, it being understood that, in practice and in an advantageous manner, the apparatus comprises a considerable number of cups permitting the carrying out of a number of simultaneous analyses, as will become apparent from the following disclosure.

According to the method of the invention, the sample of liquid medium or substance to be analysed, such as for example a sample of blood plasma, is introduced into a small cylindrical or frusto-conical cup 1 the base 1a of which is shaped to serve as a circular rolling path 1b of a ball 2 disposed in the lower part of the said cup and which is actuated with a non-rotary circular movement causing a rotation of the ball about the axis of the cup, along a circular trajectory, the different phases of slowing and/or of halting of the circular movement of the said ball caused by the thickening or coagulation of the said medium or substance, for example subsequent to the introduction of a reactant or other chemical product, being ascertainable visually or, preferably, by any suitable automatic detection system.

The apparatus for measurement of coagulation time, or coagulometer, according to the invention comprises, in its most simplified form of construction: at least one cup 1 the base 1a of which is shaped to serve as a circular rolling path 1b for a ball 2 disposed in the lower part of the said cup;—an eccentric device permitting to communicate a non-rotary circular movement to the cup;—and means ensuring the guiding of the said cup during its non-rotary circular movement. The eccentric device permitting to communicate the non-rotary circular movement of the cup is, for example, constituted by a vertical drive shaft 3 the upper end of which is provided with an eccentric pin 3a mounted rotatably in a bearing 4a, with vertical axis, provided in a movable plate or base 4 carrying the cup 1 and below which is dispsed the said driving shaft. The movable plate or base 4 is disposed horizontally and it rests in the neighbourhood of its corners on four vertical flexible supports, such as four helical springs 5 fixed, by their base, on a fixed horizontal table 6, these flexible supports tending to re-assume their vertical position after flexing. The cup 1 is positioned vertically, in such a manner that the circular path of movement 1b formed in its base is disposed in a plane which is horizontal or near to horizontal, this cup being rested or being fixed, by its upper rim 1c, on the edge of a circular opening 4b provided in a support plate which is constituted by the base 4 in the extremely simplified example of construction illustrated in FIGS. 1 and 2.

Accordingly, it will be seen that the placing into rotation of the shaft 3 permits the communication of a circular movement to the movable base 4 and to the cup 1 carried by the latter, but it is a non-rotary movement, because the springs 5 opposes rotary movement of the said base whilst guiding it during its circular movement.

The non-rotary circular movement of the cup 1 has the effect of actuating a rotation of the ball 2 in the base of the said cup in a circular path, the said ball rolling, during this movement, on the circular rolling path 1b.

When the liquid sample of medium or substance to be analysed (blood plasma for example in the base of analyses of the time of coagulation of blood or prothrombin) is introduced into the cup 1 provided with the ball 2, this latter is immersed in the liquid substance and pursues its rotary path in the base of the said cup.

The gradual thickening of the liquid medium or substance, for example following the introduction of a reactant (thromboplastine or the like in the case of measurement of the time of coagulation of blood or of blood plasma) causes firstly a progressive slowing of the speed of the rotary running of the ball, then a complete halting of this latter, this deceleration or this halting being ascertainable visually or, in a much preferred manner, by means of any appropriate detection system, disposed below the cup or laterally with respect to this latter.

A very important advantage offered by the method of the invention is that it permits the construction of coagulometers by means of which it is possible to carry out, in an entirely automated manner, numerous simultaneous analyses.

A non-limiting example of construction of a coagulometer of this kind is described below in the present disclosure, with reference to FIGS. 3 to 6. This coagulometer comprises a fixed horizontal table 6 of rectangular or other shape. On this fixed table there is mounted a movable base 4 which is coupled to this latter by means of four vertical flexible supports such as, for example, four helical springs 5 coupling the said table to the said base, these flexible supports being, preferably, disposed at the corners or in the region of the corners of the said movable base.

An eccentric (not shown), for example of the kind of that which is shown in FIGS. 1 and 2, permits the communication of a non-rotary circular movement to the base 4 and to the various members installed on this latter, the driving in rotation of this eccentric being obtained by means of an electric motor and a reducer, or by any other suitable means (not shown).

On the movable base are mounted the plate of cups 7 and the members for detection of movement of the balls, for example disposed below this latter and carried by one or more rigid plates having shapes and dimensions identical to those of the said movable base.

The plate of cups can be constituted by a plate of plastics material comprising a plurality of circular openings serving to receive removable cylindrical or frustoconical cups provided with an upper rim by means of which they rest or are fixed on the edge of the said openings.

However, in a particularly interesting manner, the plate and the cups could be moulded in a single piece, for example in a plastics material or other material which is transparent or permeable to light rays or other rays, in such a manner as to constitute a monobloc plate of cups composed of a relatively large number of cups 1 (40 cups in the example shown in FIG. 3) disposed in several parallel lines.

It is thus possible to standardise the plates of cups.

On the other hand, the plates of cups can be prepared in advance and delivered ready for use to the laboratories which use them. In this case, the balls are placed in advance in the chambers or cups 1, the upper openings of which are closed by means of detachable parallel tapes 8 after sterilisation of the plats of cups provided with their balls. It will be seen that, in this manner, it is possible, according to needs, to open only a part of the cups of a plate of cups, by only detaching the closing tapes 8 of these cups. Thus, according to FIG. 3, the two central lines of cups are shown provided with their detachable closure 8.

The balls 2 are made of a material appropriate to the nature of the detection system with which the apparatus is equipped. For example, when the detection system of the coagulometer comprises detectors utilising the optical-electronic effect, as is the case for the apparatus illustrated in FIG. 3, the balls 2 are made of a material opaque or impermeable to the rays (luminous or other) emitted by the source of rays used to act on the detectors, whilst the cups 1, or at least a partion of the base 1a or of the lateral wall of these latter, is made of a material transparent or permeable to the luminous beam or other ray provided by the emitter source.

The plate of cups 7 and the movable base 4 are provided with complementary assembly means, permitting the removable installing of the said plate of cups on the said movable base. These means are, for example, constituted on the one hand by columns 9 provided on at least two opposite sides of the movable base, and on the other hand by lateral recesses 10 of the plate of cups and in which are engaged the upper ends of the said columns, when the said plate of cups is installed on the said base.

In this position, the circular rolling paths 1b constituted by the base of the chambers or cups 1 of the plate of cups 7 are disposed in a plane which is horizontal or close to horizontal.

Figure 5:
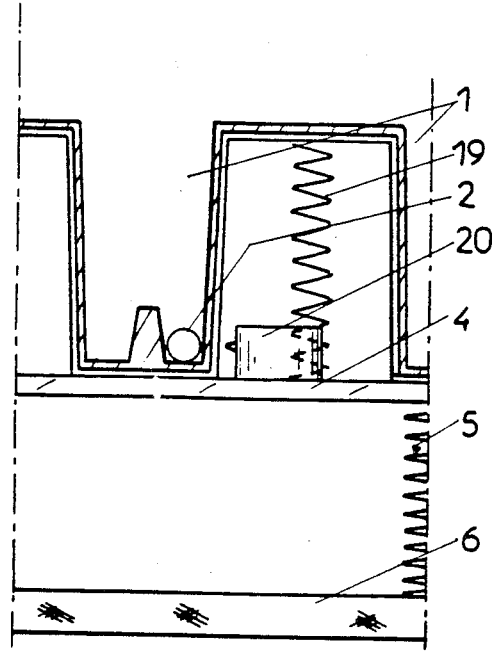
FIG. 5 is a partial view, in elevation and in section, of another variation of construction of the coagulometer, the detectors of the detection system of which are disposed laterally with respect to the cups.
Figure 6:
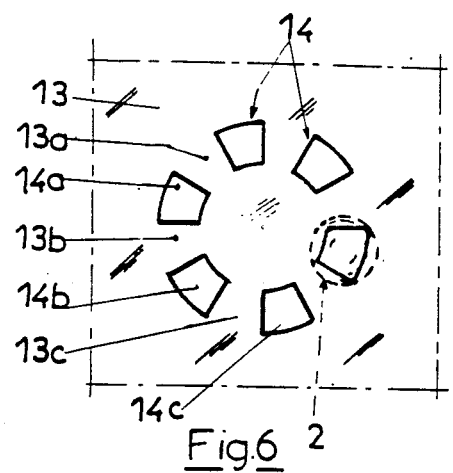
FIG. 6 is a partial view from below, showing an example of the distribution of the alternately transparent and opaque areas of the screen interposed between the base of the cups and the detectors of the apparatus, in accordance with an example of construction of the optical detection system provided.

The coagulometer comprises an automatic detection system which can be of various types (optical, fibre optical, magnetic, capacitative or other). The detectors of this detection system can, according to the nature of this latter, be placed below (FIGS. 3 and 4) the orbital space necessary to the rotary movement of the balls, or laterally with respect to this orbital space (FIG. 5).

The detection system comprises a plurality of individual detection members coupled to a chronometric reading apparatus or other recording or analysing apparatus.

Each individual detection member permits the detection of the different variations of movement of the ball disposed in the interior of this cup, from the commencement of its slowing until the complete halting of its rotation. There is illustrated, in FIG. 3, an example of construction of a detection system comprising a source of rays (luminous or other) and detectors utilising an optical-electronic effect and permitting to record and to transmit variations of electrical potential generated by the movement of the balls disposed between the said source of rays and the said detectors.

This system comprises a plurality of detectors 11, for example constituted by receiver diodes or photoconductive cells disposed in such a manner that below the base of each cup 1 of the plate of cups 7 there is a receiver diode. The detectors 11 such as receiver diodes are advantageously carried by a rigid plate 12, of insulating material, in which are incorporated the circuits and the means for connection of the said detectors to the chronometric reading apparatus or other recording apparatus.

Between the orbital space necessary for the rotary movement of each ball 2 and the receiver diode or other photoconductive cell 11 serving for the detection of the variations of movement of this ball is disposed a screen opaque to the rays (monochromatic light or white light, for example) intended to be received by the said diode or photoconductive cell, this screen comprising at least one area transparent to the said rays disposed below a portion of the circular rolling path 1b of each cup 1.

In accordance with the manner of construction illustrated in FIGS. 3 and 4, a screen 13 is disposed between the base of the cups 1 of the assembly of cups 7 and the assemby of subjacent receiver diodes or photoconductive cells 11, this screen comprising areas 14 transparent to the said rays and being disposed below the circular rolling paths 1b of the balls 2. These transparent areas 14 preferably have a radial orientation with respect to the aligned axes of the cups and of the receiver diodes.

There can be provided, between each rolling path 1b and each receiver diode 11, a single transparent area 14 having for example the shape of a portion of a circular crown (FIG. 3) or a plurality of transparent areas 14a, 14b, 14c . . . , having the shape of sectors or segments of a circular crown and separated by opaque areas 13a, 13b, 13c..., (FIG. 6) this latter arrangement permitting extremely precise measurements of the slowing down or of the variation of speed of rotation of the ball.

The transparent areas 14 can be constituted by simple openings formed in the plate constituting the screen 13.

The plate 12 carrying the receiver diodes 11 and the plate constituting the screen 13 are fixed rigidly to the movable base 4, for example by means of bolts the stems 15 of which pass through aligned openings provided at the corners of the said plates. Spacers 16 can be placed between the plates 12 and 13 in order to provide a certain spacing between these latter and avoid the crushing of the receiver diodes 11 or other photoconductive cells.

It will be seen that when the plate of cups 7 is installed on the base, the said plate of cups, the screen 13, the plate of diodes 11, 12, and the said base, are all immobilised one with respect to the other and form a compact assembly which can be activated with a non-rotary circular movement by means of the eccentric 3–3a.

Figure 7:
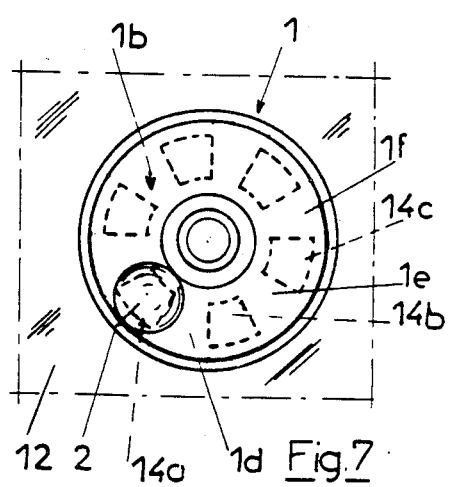
FIG. 7 is a partial view, in plan, showing an example of arrangement of the base of the cups provided with alternately transparent and opaque areas, according to a variation of construction of the optical detection system with which the coagulometer is provided.

The screen provided with one or more transparent areas can likewise be constituted by the portion of wall of each cup disposed between the orbital space necessary to the rotary movement of the ball and the detector of the detection system and, for example, as is shown in FIG. 7, by the portion of the base of the said cup which constitutes the circular rolling path 1b of the said ball. Such an arrangement permits the simplification of the construction of the apparatus, by the elimination of the plate 13.

According to this manner of construction, the opaque plate or plates 1d, 1e, 1f..., and the transparent area or areas 14a, 14b, 14c..., provided in the base 1a of the cups 1, can be obtained during the moulding of the said cups, or attaching by glueing or otherwise on the said base, subsequently to moulding.

The optical detection system further comprises a source of rays (monochromatic light, white light, for example) designated as a whole by the reference 17 in FIG. 3 and disposed above the movable assembly constituted by the base 4, the detection system 11—12—13—14, and the cups 1.

As indicated above, the detection system can also be constituted by a plurality of magnetic detectors. In this case, the detectors 20 can be installed on the movable base 4 and disposed laterally with respect to the orbital space necessary to the rotary movement of the balls, as is shown in FIG. 5, in such a manner as to record each passage of the balls in front of the said detectors.

The apparatus in accordance with the invention is provided with a device permitting the automatic introduction of liquid media or substances to be analysed, and reactants, into the cups 1. This device, which is designated by the reference 18 in FIG. 3, comprises a head which can move above the assembly of cups 1 and which is provided with a plurality of nozzles 18a permitting the simultaneous introduction of a plurality of samples of liquid substance or of doses of reactants into a corresponding number of cups 1 disposed in alignment.

The placing into operation of the device for the introduction of the substance to be analysed and/or of reactant starts the operation of the chronometric instrument or other recording apparatus.

There is no description in detail of the chronometrical instrument, the source of rays and the device for introduction of the media to be analysed and/or of reactants, which could be of various known kinds.

It is readily possible to see the operation of the apparatus of the invention which is disclosed hereinafter with reference to the manner of construction illustrated in FIG. 3.

When the assembly constituted by the base 4, the detection system 11—12—13—14 and the plate of cups 7 is actuated with a non-rotary circular movement by means of the eccentric 3–3a, the balls 2 disposed in the cups are driven in rotation along a circular path about the axis of the said cups, whether or not there is the product to be analysed alone, or the reactant alone, in the bottom of these latter.

As indicated, the introduction of the reactant, or the liquid medium to be analysed, with the aid of the automatic introduction device 18, starts up the operation of the chronometric instrument or other recording apparatus receiving the signals provided by the detectors.

In a first period, the ball 2 of each analysis unit passes successively and regularly above the transparent and opaque areas of the screen 13 and periodically intercepts, partially or completely, the luminous beam or other beam of rays emitted by the source of rays and reaches the receiver diode 11. These regular periodic passes cause regular variations of the electrical potential of the said receiver diode, which are transmitted to the reading system of the chronometric apparatus of other recording apparatus, and are transformed into regular curves constituted by an alternation of crests and hollows; the movement of rotation of the ball being uniform, the period which separates two successive peaks or summits or two successive hollows is constant.

The process of coagulation or of formation of the coagulum which is perceived as a gradual thickening of the blood plasma or other medium brings about a progressive slowing of the circular movement of the ball until there is complete halting of the latter. This progressive slowing causes a modification of the characteristics of variations of electrical potential at the receiver diode, and these give rise, on the reading system of the recording apparatus, to an increase of the time between two successive peaks or hollows.

By reason of the method and of the apparatus of the invention, it is possible to record all of the variations of the speed of rotation of the ball during the process of coagulation, and this permits new and precise analyses of this process.

The halting of movement of rotation of the ball brings about the elimination of variations of electrical potential at the receiver diode, and this situation causes the termination of the chronometric and/or recording unit associated with the detection unit concerned.

The coagulometer according to the invention can likewise comprise a heating plate, provided with openings and thermostatically controlled, for the reception of the cups. This plate disposed below the cups is fixed rigidly to the movable base 4. This plate could be independent or constituted by the screen plate 13 provided with resistances 19 (FIG. 4) and equipped with a thermostat. When the nature of the detection system permits, it can also be constituted directly by the movable base 4 arranged and equipped in this manner.

I claim:

1. A method, for ascertaining the progress of coagulation of a sample of liquid, comprising the steps of:

(i) introducing the sample into a cup having its base shaped to form an endless path for rolling of a ball disposed in said cup, (ii) imparting to the cup, with the ball and sample therein, a constant non-rotary circulating motion to cause the ball to roll, in the liquid, in said path, and (iii) detecting the occurrence of a slowing of the rolling of the ball resulting from thickening of the liquid.

2. The method claimed in claim 1 wherein the endless path is in a substantially horizontal plane, and wherein said step of detecting the occurrence of slowing of the rolling of the ball is performed by a detector means disposed adjacent to the cup.

3. The method claimed in claim 2 wherein said detecting step comprises passing rays through a transparent area, of a screen, aligned with a portion of the rolling path of said ball, and detecting variations of passage of the rays through said transparent area due to successive passes of the ball with a detector means generating correspondingly varying electrical potentials.

4. A coagulometer comprising:

(a) a cup to receive a sample of liquid, said cup including a base shaped to provide an endless rolling path for a ball;

(b) a ball disposed in said cup and rollable on said path;

(c) a base structure;

(d) guiding means interconnecting said base structure and said cup and permitting motion of the cup relative to said base structure;

(e) driving means connected to said cup for imparting to the cup a non-rotary circulating motion urging said ball to travel along said endless path.

5. A coagulometer, as claimed in claim 4, wherein said endless path is substantially horizontal, and further comprising detector means, for detecting movement of the ball along said path, disposed below said path.

6. A coagulometer, as claimed in claim 4, wherein said endless path is substantially horizontal, and further comprising detector means, for detecting movement of the ball along said path, disposed laterally of said path.

7. A coagulometer, as claimed in claim 5, comprising a source of rays disposed above said cup and arranged to project rays through said endless path for detection by said detector means.

8. A coagulometer, as claimed in claim 7, comprising an opaque screen positioned between said endless path and the detector means, said opaque screen including at least one area transparent to said rays.

9. A coagulometer, as claimed in claim 8, wherein said opaque screen is the base of the cup.

10. A coagulometer, as claimed in claim 8, wherein said opaque screen is a member disposed between the base of the cup and the detector means.

11. A coagulometer, as claimed in claim 4, wherein said guiding means comprises a movable plate to receive said cup, and flexible support means interconnecting said movable plate and said base structure.

12. A coagulometer, as claimed in claim 4, comprising thermostatically-controlled heating means for said cup.

* * * * *